(12) United States Patent
Matthys

(10) Patent No.: US 8,114,093 B2
(45) Date of Patent: Feb. 14, 2012

(54) TARGETING DEVICE

(75) Inventor: Romano Matthys, Fideris (CH)

(73) Assignee: Synthes USA, LLC, West Chester, PA (US)

( * ) Notice: Subject to any disclaimer, the term of this patent is extended or adjusted under 35 U.S.C. 154(b) by 1578 days.

(21) Appl. No.: 11/331,896

(22) Filed: Jan. 13, 2006

(65) Prior Publication Data
US 2006/0161168 A1    Jul. 20, 2006

(51) Int. Cl.
*A61B 17/60* (2006.01)
(52) U.S. Cl. .......................... 606/104; 606/96
(58) Field of Classification Search ............ 606/53, 606/65, 66, 67, 69, 70, 71, 86, 96–98, 99, 606/103, 104, 281–299, 915, 86 R
See application file for complete search history.

(56) References Cited

U.S. PATENT DOCUMENTS

| | | | | |
|---|---|---|---|---|
| 4,465,065 A * | 8/1984 | Gotfried | | 606/65 |
| 4,622,959 A * | 11/1986 | Marcus | | 606/64 |
| 4,733,654 A * | 3/1988 | Marino | | 606/64 |
| 4,911,153 A * | 3/1990 | Border | | 606/98 |
| 5,078,719 A * | 1/1992 | Schreiber | | 606/87 |
| 5,334,192 A * | 8/1994 | Behrens | | 606/96 |
| 5,403,321 A * | 4/1995 | DiMarco | | 606/96 |
| 5,620,449 A * | 4/1997 | Faccioli et al. | | 606/98 |
| 5,728,128 A * | 3/1998 | Crickenberger et al. | | 606/97 |
| 5,916,219 A * | 6/1999 | Matsuno et al. | | 606/88 |
| 5,947,970 A * | 9/1999 | Schmelzeisen et al. | | 606/70 |
| 6,056,756 A * | 5/2000 | Eng et al. | | 606/87 |
| 6,090,114 A * | 7/2000 | Matsuno et al. | | 606/88 |
| 6,102,911 A * | 8/2000 | Faccioli et al. | | 606/54 |
| 6,120,511 A | 9/2000 | Chan | | |
| 6,340,361 B1 * | 1/2002 | Kraus et al. | | 606/59 |
| 6,342,056 B1 * | 1/2002 | Mac-Thiong et al. | | 606/96 |
| 6,344,043 B1 * | 2/2002 | Pappas | | 606/96 |
| 6,746,453 B2 * | 6/2004 | Deloge et al. | | 606/98 |
| 6,926,720 B2 * | 8/2005 | Castaneda | | 606/98 |
| 7,077,847 B2 * | 7/2006 | Pusnik et al. | | 606/96 |
| 7,101,181 B2 * | 9/2006 | Bompard et al. | | 433/75 |
| 7,144,399 B2 * | 12/2006 | Hayes et al. | | 606/98 |
| 7,175,631 B2 * | 2/2007 | Wilson et al. | | 606/97 |
| 7,416,553 B2 * | 8/2008 | Patel et al. | | 606/246 |
| 7,425,213 B2 * | 9/2008 | Orbay | | 606/62 |
| 7,431,731 B2 * | 10/2008 | Kitchens | | 606/281 |
| 7,481,815 B2 * | 1/2009 | Fernandez | | 606/97 |
| 7,488,328 B2 * | 2/2009 | Gotfried | | 606/99 |
| 7,575,578 B2 * | 8/2009 | Wetzler et al. | | 606/96 |
| 2006/0200157 A1 * | 9/2006 | Orbay et al. | | 606/87 |

FOREIGN PATENT DOCUMENTS

| | | |
|---|---|---|
| DE | 200 19026 | 5/2002 |
| EP | 0468192 | 1/1992 |
| EP | 1 275 348 | 1/2003 |

* cited by examiner

*Primary Examiner* — Thomas C. Barrett
*Assistant Examiner* — Christopher Beccia
(74) *Attorney, Agent, or Firm* — Fay Kaplun & Marcin, LLP

(57) ABSTRACT

The invention relates to an aiming, or targeting, device which is used to guide and place longitudinal bone fixing means in a predetermined direction with respect to a bone fixing device. The aiming device includes securing means, which can be detachably secured to a bone fixing device, a first centering part, which can be placed on the bone fixing device, and a second centering part, which is arranged at a distance from the first centering part. Both of the centering parts include at least one pair of guiding elements which are arranged in a coaxial manner in relation to each other.

18 Claims, 1 Drawing Sheet

TARGETING DEVICE

RELATED APPLICATION DATA

The present application is a continuation of the U.S. National Stage designation of co-pending International Patent Application No. PCT/CH2003/000467 filed Jul. 14, 2003. the entire content of which is expressly incorporated herein by reference thereto.

FIELD OF THE INVENTION

The invention relates to a targeting device for use with bone fixation devices.

BACKGROUND OF THE INVENTION

In the case of bone fixation devices, particularly bone plates, the problem arises of fastening these devices by means of suitable, longitudinal bone fixation means, such as bone screws, bone wires, bone pins or Kirschner wires, to the bone fragments, so that the longitudinal bone fixation means have a particular direction with respect to the bone fixation device, especially, a specific angle to the bone fixation device. This problem arises principally in the case of bone plates, which consist of a plastic and do not yet have any plate boreholes, for example, the bone plate of International patent publication WO 01/012081.

A device with a centering sleeve for setting the bone fixation means at a plastic plate is known from the German publication DE-U 200 19 026. This known device comprises a targeting bracket, at which a bone plate can be attached by fastening means, and a guiding part, which can be shifted at the targeting bracket and shifted and rotated relative to the bone plate. The single guiding part is tubular in construction and serves to center and guide surgical instruments and/or implants. The tubular configuration of the guiding part permits only one bone fixation means to be accommodated. In the event that, for example, several Kirschner wires are to be set at one bone plate, the guiding part must be shifted and aligned once again with respect to the targeting bracket for each Kirschner wire, which is to be set. This results in the expenditure of much time for setting, for example, four Kirschner wires.

The invention is to provide a remedy here. It is an object of the invention to create a targeting device, which, on the one hand, permits drilling instruments or drill guide sleeves to be positioned in a previously determined direction with respect to the bone and/or, on the other, permits the surgeon to bring longitudinal bone-fixation means (Kirschner wires) into the bone in a previously determined direction, preferably in a direction in which they diverge from one another.

SUMMARY OF THE INVENTION

Pursuant to the invention, this objective is accomplished by a targeting apparatus for guiding fixation elements relative to a bone fixation device comprising a targeting bracket formed of a connecting portion having a first end and a second end, the first end configured and dimensioned for attachment to the bone fixation device, e.g., bone plate, and a handle portion disposed at the second end of the connecting portion. A first centering part is disposed at the first end of the connecting portion, the first centering part having a first guide for aligning a longitudinal bone fixation element relative to the bone fixation device. A second centering part is disposed on the handle portion, spaced from the first centering part, the second centering part having a second guide for aligning a longitudinal bone fixation element relative to the bone fixation device, and n the first and second guides are coaxial with one another and form a first guide pair.

The advantages, achieved by the invention, are to be seen essentially therein that, due to the inventive targeting device:
the longitudinal bone fixation means can be positioned precisely by the surgeon without previously having to implant a Kirschner wire in the bone;
the position of the Kirschner wires is predetermined clearly by the surgeon without previously having to implant a Kirschner wire in the bone;
the position of the Kirschner wires is predetermined clearly by the anatomy of the humerus and the position selected underneath the axillary nerve and becomes reproducible due to the targeting device (this is not the case with a targeting device, which permits the user to select the positioning freely); and
the bone fixation element can be implanted as well as explanted.

In a preferred embodiment, the two centering parts have at least two pairs of mutually coaxial guides. Each pair of guides comprises a guide in the first centering part, which is disposed at the front end of the targeting bracket and can be connected with the bone fixation device, and a guide in the second centering part, which is disposed at the handle of the targeting bracket. Preferably, the pairs of guides are constructed so that the axes of the different pairs of guides diverge. By these means, the advantage can be achieved that several bone fixation means (Kirschner wires) can be implanted without having to adapt and adjust the targeting device once again to the directions of the individual Kirschner wires. Preferably, the bone fixation device is constructed as a bone plate.

In a different embodiment, the two centering parts and the targeting bracket are constructed so that the two centering parts at the targeting device are exchangeable. By these means, the further advantage can be obtained that the guiding pairs or longitudinal bone fixation agents can be set at angles determined in advance, for example, with respect to a bone plate, by one set of centering pairs with different orientations.

In yet another embodiment, the guides are fixed with respect to the centering parts, so that undesirable shifting of the guides relative to the centering parts is not possible.

In a further embodiment, the centering parts can be connected with the targeting device only in a position defined with respect to the targeting device. On the one hand, errors in the installation of the targeting device can be excluded by this configuration and, on the other, the positions of the two centering parts can be found easily, as a result of which the installation of the targeting device is simplified appreciably.

In yet another embodiment, the targeting device comprises a two-part targeting bracket with a sleeve, suitable for accommodating the fastening means between the targeting bracket and the bone fixation means and a handle part disposed transversely to the central axis. Preferably, the first centering part is connected firmly with this sleeve, the sleeve being secured relative to the handle part against twisting about the central axis of the sleeve.

In a different embodiment, the guides in the second centering part, disposed at the handle part of the targeting bracket, are constructed as boreholes, so that the drill guide sleeves or bone fixation means, which can be introduced into the boreholes, are enclosed on the whole of the periphery and cannot be shifted laterally. The guides in the first centering part, which can be fastened, for example, to a bone plate, preferably are constructed as centering grooves, which are coaxial with the axes of the boreholes.

In yet another embodiment, the targeting device comprises one or more boreholes for accommodating longitudinal targeting aids, which preferably are constructed in the form of aiming stakes and make it easier for the surgeon to align the targeting device at the body of the patient.

The bone plates used preferably are made from PEEK, an implantable plastic with very good mechanical properties. The plate is provided with a central borehole, which is used for temporarily fixing the targeting instrument at the plate. However, due to the conical internal thread (which fits the head locking screws) in the borehole, a corresponding bone screw can also be fixed therein after the Kirschner wires have been positively located and the targeting instrument removed, in order to anchor the bone plate additionally with the bones.

BRIEF DESCRIPTION OF THE DRAWINGS

The invention is explained in even greater detail in the following by means of the partly diagrammatic representation of an example, in which.

DETAILED DESCRIPTION OF THE PREFERRED EMBODIMENTS

Figure 1:
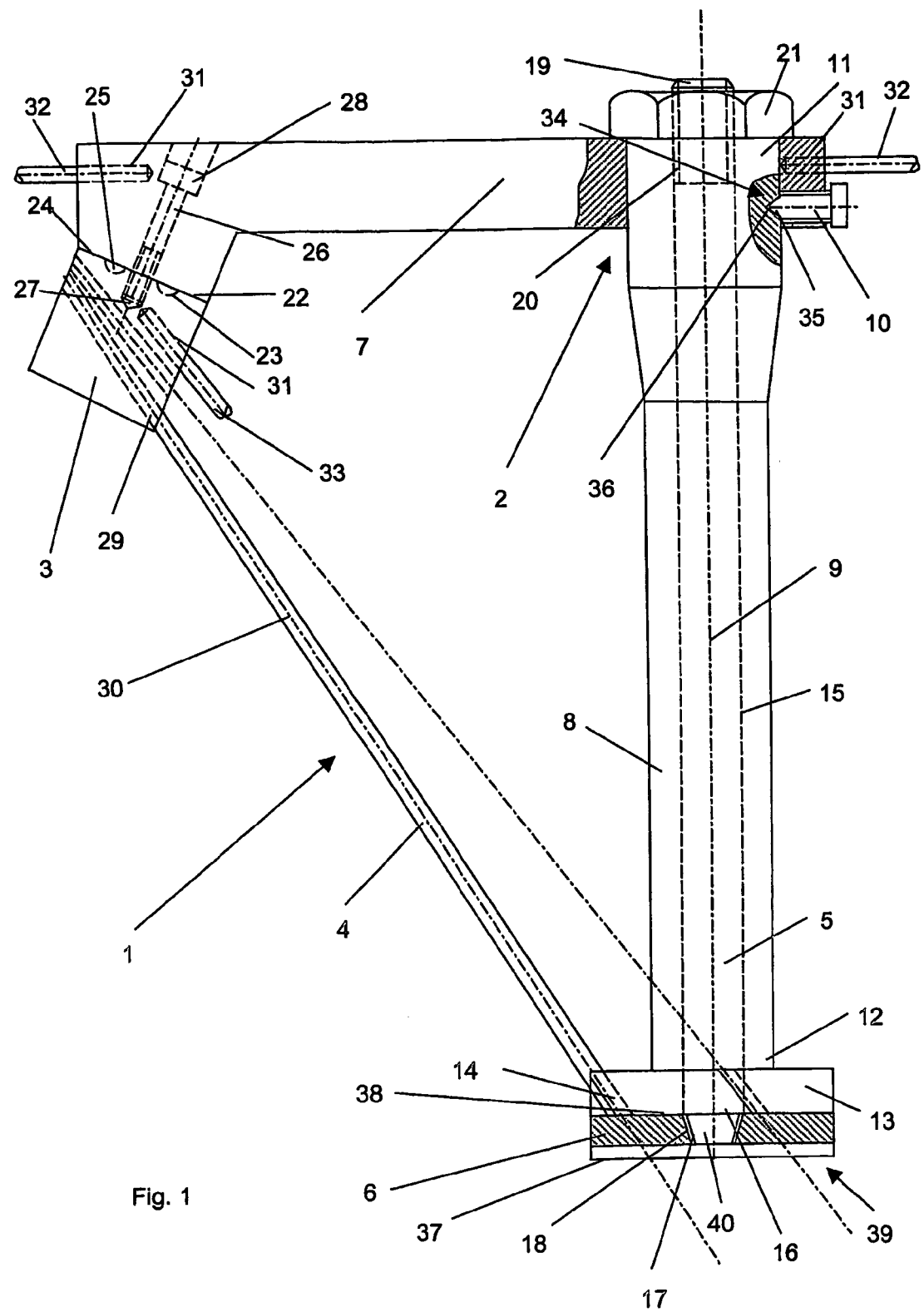
FIG. 1 shows longitudinal sections through an embodiment of the inventive targeting device.

An example of the inventive targeting device 1 is shown in FIG. 1. It comprises a two-part targeting bracket 2, a first and a second centering part 13, 3 for accommodating and guiding bone fixation elements 4, such as Kirschner wires and a fastening agent 5, which can be fastened at a bone plate 6.

The two-part targeting bracket 2 consists of a longitudinal, hollow cylindrical sleeve 8 with a central axis 9 and a handle part 7, which can be fastened at the rear end 11 of the sleeve 8 by means of a screw 10 and is disposed transversely to the central axis 9. The first centering part 13 is mounted at the front end 12 of the sleeve 8 and comprises guides 14, which are disposed skew with respect to the central axis 9 and are in the form of centering grooves for the bone fixation elements 4, so that the bone fixation elements 4, before they penetrate into the bone plate 6, are passed through the guides 14 of the first centering part 13. The central borehole 15 of the sleeve 8 also passes through the first centering part 13, so that the fastening agent 5, which is also cylindrical, can be passed through the central borehole 15 coaxially with the central axis 9. The sleeve 8 is locked in place at the handle part 7 so that it cannot rotate about the central axis 9. Security against rotation 34 is realized by the screw 10, which can be screwed into the handle part 7 and the tip 35 of which can be taken up in a depression 36 at the sleeve 8, so that, after the screw 10 is locked in place, the sleeve 8, together with the centering part 13, is immobilized in the handle part 7.

The tip 16 of the fastening agent 5 is provided with an external conical thread 17, which can be screwed into a complementary internal thread 18 in the borehole 40 provided in the bone plate 6. By means of a nut 21, which can be screwed over an external thread 20 provided at the rear end 19 of the fastening agent 5 and rests on the handle part 7, the fastening agent 5, together with the bone plate 6, is fastened to the targeting bracket 2.

The second centering part 3 is constructed as a rectangular block and provided at its side surfaces 22, which are directed toward the targeting bracket 2, with three spherical depressions 23, whereas the targeting bracket 2, at its side surface 24 directed against the second centering part 3, has three spherical elevations 25, which are complementary to the depressions 23. The second centering part 3 is secured against twisting relative to the targeting bracket 2 by the elevations 25, which engaged the depressions 23. The second centering part 3 is fastened by means of a screw 26, which can be screwed into a corresponding borehole 27 in the second centering part 3 having an internal thread and the screw head 28 of which lies in contact with the handle part 7. Furthermore, the second centering part 3 comprises four guides 29 in the form of boreholes, which pass through the second centering part 3 transversely to the central axis 9 and the axes 30 of which extend transversely to the central axis 9 and are skew relative to one another. The guides 29 are disposed so that their axes 30 are aligned with the guides 14 in the first centering part 13, which are constructed as centering grooves, so that the bone fixation elements 4, when pushed through the guides 29, are guided in the guides 29, which are disposed remote from the bone plate 6, as well as in the guides 14, which are located close to the bone plate 6.

Furthermore, boreholes 31 for accommodating targeting aids 32, 33 in the form of aiming stakes are mounted at the centering part 3 as well as at the handle part 7. The boreholes 31 are aligned so that the first targeting aid 32, which can be mounted at the handle part 7, is perpendicular to the central axis 9, while the second targeting aid 33, which can be mounted at the centering part 3, is aligned in the direction of the line connecting the centering part 3 and the centering part 13. The targeting aids 32, 33 enable the surgeon to align the targeting device 1 with respect to the bone that is to be treated.

The use and function of the inventive targeting device is described in greater detail below by means of the surgical method for the proximal humerus:

A) Implantation:

To begin with, the fractured, proximal humerus is repositioned roughly over the soft parts.

2-3 cm skin incision underneath the axillary nerve at the proximal humerus;

Prepare the way bluntly with the index finger up to the shaft.

Guide the targeting device with the mounted plate up to the shaft and position it appropriately with the help of the external targeting wires.

Anchor the targeting device in the specified position at the shaft of the humerus with a 2.5 mm K wire.

Introduce the drill guide bushing into the marked borehole in the targeting instrument and advance up to the plate with a movement, oscillating circularly about the longitudinal axis.

Introduce 2.0 mm spiral drill. Before the drilling process, check once more the alignment of the targeting instrument along the longitudinal axis and, if necessary, correct. If the position along the longitudinal axis and the height are correct, the cortex in the shaft region is bored.

Remove 2.0 mm drill and introduce first 2.5 mm K wire up to the fracture line. Leave drill guide sleeve in the targeting instrument and use the second drill guide sleeve for the next Kirschner wire.

Use same procedure (pre-bore and introduce the K wire up to the fracture line) for the remaining three K wires.

Definitive reposition of the fracture and subsequent threading of Kirschner wires into the end position selected by the surgeon.

Remove targeting device from the plate.

Sever the protruding ends of the Kirschner wires with the trimming device as close as possible to the plate surface.

The ends of the Kirschner wires now protrude approximately 8-10 mm from the plate surface.

End of osteosynthesis.

B) Explantation:

2-3 cm skin incision below the axillary nerve at the proximal humerus.

Prepare the way bluntly with the index finger up to the shaft.

Guide the targeting device up to the plate and fix once more to the plate with the fastening screw.

Introduce the extraction bolt into the targeting device up to the end of the Kirschner wire.

Rotate extraction bolt counterclockwise and remove the Kirschner wire manually. Follow same procedure for the remaining Kirschner wires.

Remove the targeting device.

End of the explantation.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed is:

1. A targeting apparatus for guiding fixation elements relative to a bone fixation device comprising:
    a connecting sleeve having a first end and a second end, the first end configured and dimensioned for attachment to the bone fixation device;
    a handle portion having a first end disposed at the second end of the connecting sleeve and a second free end;
    a first centering part disposed at the first end of the connecting sleeve, the first centering part including a guide surface which, when the connecting sleeve is attached to the bone fixation device in a desired configuration, covers a proximal surface of the bone fixation device, the guide surface including a plurality of first guide channels; and
    a second centering part disposed on the second free end of the handle portion, spaced from the first centering part, the second centering part having a plurality of second guide channels, each of which is coaxially aligned with a corresponding one of the first guide channels to define a path along which a bone fixation element is to be inserted through the bone fixation device into the bone.

2. The apparatus of claim 1, wherein the bone fixation device is a bone plate.

3. The apparatus of claim 2, wherein at least a portion of the first centering part contacts the bone fixation device.

4. The apparatus of claim 1, further comprising a third guide on the first centering part and a fourth guide on the second centering part, the third and fourth guides coaxial with one another to align a longitudinal bone fixation element relative to the bone fixation device and form a second guide pair.

5. The apparatus of claim 4, wherein the first guide pair and the second guide pair define two different, non-parallel directions.

6. The apparatus of claim 1, wherein the connecting sleeve is detachably fastened to the bone fixation device.

7. The apparatus of claim 1, wherein the first and second centering parts are detachably connected to the targeting apparatus.

8. The apparatus of claim 1, wherein the first and second centering parts are configured for attachment to the targeting apparatus in only a single orientation.

9. The apparatus of claim 1, wherein the connecting sleeve has a central axis configured to receive a fastening element, and the handle portion is disposed transversely to the central axis.

10. The apparatus of claim 9, wherein the first centering part is connected to the sleeve, and the sleeve is secured against rotation about the central axis relative to the handle part.

11. The apparatus of claim 4, wherein the guides in the second centering part are boreholes having a first set of axes.

12. The apparatus of claim 11, wherein the guides in the first centering part are centering grooves coaxial with the first set of axes.

13. The apparatus of claim 1, wherein the second centering part includes a plurality of depression that mate with corresponding elevations on the handle portion.

14. A targeting apparatus for guiding fixation elements relative to a bone plate comprising:
    a connecting sleeve having a first end and a second end, the first end configured and dimensioned for attachment to the bone plate;
    a handle having a first end disposed at the second end of the connecting sleeve and a second free end;
    a first centering part disposed at the first end of the connecting sleeve, the first centering part including a guide surface which, when the connecting sleeve is attached to the bone fixation device in a desired configuration, covers a proximal surface of the bone fixation element, the guide surface including a plurality of first guide channels; and
    a second centering part disposed on the second free end of the handle, spaced from the first centering part, the second centering part having a plurality of second guide channels, each of which is coaxially aligned with a corresponding one of the first guide channels.

15. The apparatus of claim 14, further comprising: a third guide on the first centering part for aligning a longitudinal bone fixation element relative to the bone plate in a second direction; and a fourth guide, coaxial with the third guide, on the second centering part for aligning a longitudinal bone fixation element relative to the bone plate in the second direction.

16. The apparatus of claim 14, wherein the first and second centering parts are detachably connected to the targeting apparatus.

17. The apparatus of claim 1, wherein the connection sleeve defines a central bore further comprising a fastening element, the fastening element including a first end configured for coupling to the bone fixation device and a second end configured for coupling to the second end of the connection sleeve.

18. The apparatus of claim 14, wherein the connection sleeve defines a central bore further comprising a fastening element, the fastening element including a first end configured for coupling to the bone fixation device and a second end configured for coupling to the second end of the connection sleeve.

* * * * *

UNITED STATES PATENT AND TRADEMARK OFFICE
CERTIFICATE OF CORRECTION

PATENT NO. : 8,114,093 B2  
APPLICATION NO. : 11/331896  
DATED : February 14, 2012  
INVENTOR(S) : Matthys Page 1 of 1

It is certified that error appears in the above-identified patent and that said Letters Patent is hereby corrected as shown below:

In the Title Page, Item [63] insert the following information:

--Related U.S. Application Data

Continuation of the Application No. PCT/CH2003/000467 filed July 14, 2003--.

Signed and Sealed this
Seventeenth Day of April, 2012

David J. Kappos
*Director of the United States Patent and Trademark Office*